(12) United States Patent
Takakura et al.

(10) Patent No.: US 6,881,720 B1
(45) Date of Patent: Apr. 19, 2005

(54) **ANTIMICROBIAL PROTEIN FROM *LYOPHYLLUM SHIMEJI***

(75) Inventors: Yoshimitsu Takakura, Shizuoka (JP); Shigeru Kuwata, Shizuoka (JP); Yasuhiro Inoue, Shizuoka (JP)

(73) Assignees: Japan Tabacco Inc., Tokyo (JP); Corporate Juridical Person, Society for Techno-Innovation of Agriculture, Forestry and Fisheries, Tokyo (JP)

( * ) Notice: Subject to any disclaimer, the term of this patent is extended or adjusted under 35 U.S.C. 154(b) by 111 days.

(21) Appl. No.: 09/856,327

(22) PCT Filed: Sep. 20, 2000

(86) PCT No.: PCT/JP00/06404

§ 371 (c)(1), (2), (4) Date: Jun. 7, 2001

(87) PCT Pub. No.: WO01/21657

PCT Pub. Date: Mar. 29, 2001

(30) Foreign Application Priority Data

Sep. 21, 1999 (JP) .......................................... 11-267238

(51) Int. Cl.$^7$ ................................................ A61K 38/00
(52) U.S. Cl. ........................................................ 514/12
(58) Field of Search .................... 514/12, 23; 536/23.1, 536/23.2, 23.4, 23.7, 23.74, 24.3, 24.32; 530/300, 350; 435/69.1, 320, 320.1, 91.1, 440, 480, 471, 483, 325, 252.3, 252.33, 254.11; 47/1.1; 800/297

(56) References Cited

U.S. PATENT DOCUMENTS 5,712,139 A * 1/1998 Nishimura et al. .......... 435/190
6,291,648 B1 * 9/2001 Kawamura et al. ......... 530/371
6,559,294 B1 * 5/2003 Griffais et al. ............. 536/23.1

FOREIGN PATENT DOCUMENTS

WO   WO94/11511   5/1994
WO   WO95/04754   2/1995

OTHER PUBLICATIONS

Lazar E, Watanabe S, Dalton S, Sporn MB. Transforming growth factor alpha: mutation of aspartic acid 47 and leucine 48 results in different biological activities. Mol Cell Biol. Mar. 1988;8(3):1247–52.*

Bowie Ju, Reidhaar–Olson JF, Lim Wa, Sauer Rt. Deciphering the message in protein sequences: tolerance to amino acid substitutions. Science. Mar. 16, 1990;247(4948):1306–10.*

Qun Zhu et al., Bio/Technology, vol. 12 (1994) pp. 807–812.

Willie Lin et al., Bio/Technology, vol. 13 (1995) pp. 686–691.

Franky R.G. Terras et al., The Plant Cell, vol. 7 (1995) pp. 573–588.

Shigeru Oita et al., Biosci. Biotech. Biochem, vol. 60, No. 3 (1996) pp. 481–483.

Franky R.G. Terras et al., J. of Bio. Chem., vol. 267, No. 22 (1992) pp. 15301–15309.

Angela Schlumbaum et al., Nature, vol. 324 (1986) pp. 365–367.

Karen Broglie et al., Science, vol. 254 (1991) pp. 1194–1197.

Felix Mauch et al., Plant Physiol., vol. 88 (1988) pp. 936–942.

Marianne B. Sela–Buurlage et al., Plant Physiol., vol. 101 (1993) pp. 857–863.

* cited by examiner

*Primary Examiner*—Karen Cochrane Carlson
*Assistant Examiner*—Sheridan Snedden
(74) *Attorney, Agent, or Firm*—Birch, Stewart, Kolasch & Birch, LLP

(57) ABSTRACT

The object of the present invention is to screen and identify a novel antimicrobial protein which can inhibit the growth of plant pathogenic microorganisms at a relatively low concentration such as *Pyricularia oryzae* and *Rhizoctonia solani* causative of two major diseases causing damage to rice crops and, further, to clone the gene of this protein. According to the present invention, an antimicrobial protein which can be obtained from a fraction of an aqueous extract of *Lyophyllum shimeji* precipitated by the ammonium sulfate precipitation method, has an antimicrobial activity at least against *Rhizoctonia solani* or *Pyricularia oryzae*, and shows the presence of components of about 70 kDa and/or about 65 kDa in molecular weight in the SDS-PAGE method. A gene encoding this protein and a method of using the same are provided.

16 Claims, 2 Drawing Sheets

SEQUENCE LISTING

<160> NUMBER OF SEQ ID NOS: 12

<210> SEQ ID NO 1
<211> LENGTH: 2106
<212> TYPE: DNA
<213> ORGANISM: Lyophyllum shimeji
<220> FEATURE:
<221> NAME/KEY: CDS
<222> LOCATION: (8)..(1861)
<223> OTHER INFORMATION:

<400> SEQUENCE: 1

```
atcagcc atg tct ctc tca acc gag cag atg cta cgc gac tat cca cgg        49
        Met Ser Leu Ser Thr Glu Gln Met Leu Arg Asp Tyr Pro Arg
        1               5                   10 tct atg caa atc aac gga cag att cct aag aac gca att cac gaa aca        97
Ser Met Gln Ile Asn Gly Gln Ile Pro Lys Asn Ala Ile His Glu Thr
15                  20                  25                  30 tac gga aac gac gga gtt gat gta ttc att gca gga tct gga ccc att       145
Tyr Gly Asn Asp Gly Val Asp Val Phe Ile Ala Gly Ser Gly Pro Ile
                35                  40                  45 gga gcg acg tat gca aag ctc tgt gtt gaa gct ggt cta cgt gtt gtg       193
Gly Ala Thr Tyr Ala Lys Leu Cys Val Glu Ala Gly Leu Arg Val Val
        50                  55                  60 atg gtc gag atc gga gct gct gat agc ttc tac gct gtt aat gcc gaa       241
Met Val Glu Ile Gly Ala Ala Asp Ser Phe Tyr Ala Val Asn Ala Glu
65                  70                  75 gaa gga act gca gtt ccc tac gtt cct ggc tac cac aag aag aat gaa       289
Glu Gly Thr Ala Val Pro Tyr Val Pro Gly Tyr His Lys Lys Asn Glu
80                  85                  90 atc gag ttc cag aaa gat att gac cgc ttc gtc aat gta atc aag gga       337
Ile Glu Phe Gln Lys Asp Ile Asp Arg Phe Val Asn Val Ile Lys Gly
95                  100                 105                 110 gcc tta caa caa gtc tct gtt cct gtc aga aac cag aac gtg cct aca       385
Ala Leu Gln Gln Val Ser Val Pro Val Arg Asn Gln Asn Val Pro Thr
                115                 120                 125 ctt gat ccc gga gcc tgg agc gcg ccc cct gga agt tca gcc ata tcg       433
Leu Asp Pro Gly Ala Trp Ser Ala Pro Pro Gly Ser Ser Ala Ile Ser
        130                 135                 140 aac ggt aaa aat cct cac cag cgg gaa ttc gag aac ttg tct gcg gag       481
Asn Gly Lys Asn Pro His Gln Arg Glu Phe Glu Asn Leu Ser Ala Glu
        145                 150                 155 gcc gta acg cgt gga gtc ggc ggc atg agt acc cac tgg acg tgc tcc       529
Ala Val Thr Arg Gly Val Gly Gly Met Ser Thr His Trp Thr Cys Ser
        160                 165                 170 acg cca cgg att cat cca ccc atg gaa agt ctc ccg ggc atc ggc cgt       577
Thr Pro Arg Ile His Pro Pro Met Glu Ser Leu Pro Gly Ile Gly Arg
175                 180                 185                 190 ccg aag ctc agt aac gac ccg gca gag gac gac aaa gag tgg aac gag       625
Pro Lys Leu Ser Asn Asp Pro Ala Glu Asp Asp Lys Glu Trp Asn Glu
                195                 200                 205 ctt tat tcc gag gcc gag cgt ctc atc ggg act tcc acc aag gaa ttc       673
Leu Tyr Ser Glu Ala Glu Arg Leu Ile Gly Thr Ser Thr Lys Glu Phe
        210                 215                 220
```

-continued

| | |
|---|---|
| gac gag tca att cgg cac acc ctt gtt ctg cgc tct ttg caa gac gcg<br>Asp Glu Ser Ile Arg His Thr Leu Val Leu Arg Ser Leu Gln Asp Ala<br>        225                                230                          235 | 721 |
| tac aag gat cgt caa cgt atc ttt cgc cct ctc ccg ttg gca tgc cac<br>Tyr Lys Asp Arg Gln Arg Ile Phe Arg Pro Leu Pro Leu Ala Cys His<br>        240                                245                          250 | 769 |
| cgg ttg aag aac gcg ccg gaa tac gtc gaa tgg cac tca gca gaa aat<br>Arg Leu Lys Asn Ala Pro Glu Tyr Val Glu Trp His Ser Ala Glu Asn<br>255                          260                          265                        270 | 817 |
| ctt ttc cac tct atc tac aac gat gac aag cag aag aag ctc ttt acc<br>Leu Phe His Ser Ile Tyr Asn Asp Asp Lys Gln Lys Lys Leu Phe Thr<br>                        275                          280                        285 | 865 |
| ctg ctg acg aac cat cgc tgc aca cga ctg gcg ctt acg ggc ggg tat<br>Leu Leu Thr Asn His Arg Cys Thr Arg Leu Ala Leu Thr Gly Gly Tyr<br>        290                                295                          300 | 913 |
| gag aag aag att ggc gct gcc gag gtc agg aat cta ctg gcc acc agg<br>Glu Lys Lys Ile Gly Ala Ala Glu Val Arg Asn Leu Leu Ala Thr Arg<br>                        305                          310                        315 | 961 |
| aat cct agt tcg cag ctg gac agc tat atc atg gcg aag gta tat gta<br>Asn Pro Ser Ser Gln Leu Asp Ser Tyr Ile Met Ala Lys Val Tyr Val<br>320                          325                          330 | 1009 |
| ctg gcg tcg gga gcg atc ggc aac cca cag att ctc tat aac tcg ggc<br>Leu Ala Ser Gly Ala Ile Gly Asn Pro Gln Ile Leu Tyr Asn Ser Gly<br>335                          340                          345                        350 | 1057 |
| ttc tct ggg cta cag gtc acg cca cgc aat gac tcg ttg atc ccc aac<br>Phe Ser Gly Leu Gln Val Thr Pro Arg Asn Asp Ser Leu Ile Pro Asn<br>                        355                          360                        365 | 1105 |
| ctg ggg agg tac atc acg gag cag ccg atg gca ttt tgc cag ata gtc<br>Leu Gly Arg Tyr Ile Thr Glu Gln Pro Met Ala Phe Cys Gln Ile Val<br>                          370                          375                        380 | 1153 |
| ttg agg cag gaa ttc gtc gac agc gtg cgc gac gat cct tat gga ctg<br>Leu Arg Gln Glu Phe Val Asp Ser Val Arg Asp Asp Pro Tyr Gly Leu<br>        385                              390                          395 | 1201 |
| cca tgg tgg aaa gaa gcc gtt gct caa cat att gcc aag aac ccg aca<br>Pro Trp Trp Lys Glu Ala Val Ala Gln His Ile Ala Lys Asn Pro Thr<br>                        400                          405                        410 | 1249 |
| gat gca ctg ccc att ccg ttc cgc gat ccg gaa ccc cag gta aca acc<br>Asp Ala Leu Pro Ile Pro Phe Arg Asp Pro Glu Pro Gln Val Thr Thr<br>415                          420                          425                        430 | 1297 |
| cca ttt aca gaa gaa cac ccc tgg cac acg cag att cac cgc gat gct<br>Pro Phe Thr Glu Glu His Pro Trp His Thr Gln Ile His Arg Asp Ala<br>                        435                          440                        445 | 1345 |
| ttt tcg tac ggt gcc gtc ggt cct gag gtg gac tct cgt gtc atc gtc<br>Phe Ser Tyr Gly Ala Val Gly Pro Glu Val Asp Ser Arg Val Ile Val<br>        450                              455                          460 | 1393 |
| gac ctg cgc tgg ttt ggc gca acc gac cct gaa gca aac aac ctt ttg<br>Asp Leu Arg Trp Phe Gly Ala Thr Asp Pro Glu Ala Asn Asn Leu Leu<br>                        465                          470                        475 | 1441 |
| gtt ttc cag aac gat gtt caa gac ggg tac agt atg ccg cag ccg acg<br>Val Phe Gln Asn Asp Val Gln Asp Gly Tyr Ser Met Pro Gln Pro Thr<br>480                          485                          490 | 1489 |
| ttc aga tat cga ccc agc act gcg tca aac gtg aga gca agg aaa atg<br>Phe Arg Tyr Arg Pro Ser Thr Ala Ser Asn Val Arg Ala Arg Lys Met<br>495                          500                          505                        510 | 1537 |
| atg gcc gat atg tgc gaa gtg gcg agc aac ttg gga ggt tat ttg ccc<br>Met Ala Asp Met Cys Glu Val Ala Ser Asn Leu Gly Gly Tyr Leu Pro<br>                        515                          520                        525 | 1585 |
| acg tcc ccc ccg cag ttt atg gat cca ggc ctt gca ctt cat ctt gcg<br>Thr Ser Pro Pro Gln Phe Met Asp Pro Gly Leu Ala Leu His Leu Ala<br>        530                              535                          540 | 1633 |

```
                                                          -continued ggg act act cgc att ggc ttc gac aag gca act aca gtg gct gat aac    1681
Gly Thr Thr Arg Ile Gly Phe Asp Lys Ala Thr Thr Val Ala Asp Asn
            545                 550                 555 aac tcg ctg gtc tgg gac ttt gcc aat ctt tat gtt gca ggc aat ggc    1729
Asn Ser Leu Val Trp Asp Phe Ala Asn Leu Tyr Val Ala Gly Asn Gly
        560                 565                 570 acc atc agg acg ggc ttc ggc gag aac ccg aca ctt acg tcg atg tgc    1777
Thr Ile Arg Thr Gly Phe Gly Glu Asn Pro Thr Leu Thr Ser Met Cys
575                 580                 585                 590 cac gct atc aag agc gcg agg agc atc atc aat aca ctc aag ggt ggg    1825
His Ala Ile Lys Ser Ala Arg Ser Ile Ile Asn Thr Leu Lys Gly Gly
                595                 600                 605 act gac gga aaa aat aca ggc gag cat cgc aac ctt tgaggaagga         1871
Thr Asp Gly Lys Asn Thr Gly Glu His Arg Asn Leu
            610                 615 gcaacagcag tgtaaacaaa cgcgtcaagt ggctacttca agttgaatgc attctggtcc  1931
cctaccatgt tgatgtgtac gataggcgtt gaaagatttt gtgtattact gaacctgtac  1991
tttgtctgaa tagttatggc actatgattc atgtttaaaa aaaaaaaaaa aaaaaaaaa   2051 aaaaaaaaaa aaaaaaaaaa aaaaaaaaaa aaaaaaaaaa aaaaaaaaaa aaaaa       2106

<210> SEQ ID NO 2
<211> LENGTH: 618
<212> TYPE: PRT
<213> ORGANISM: Lyophyllum shimeji

<400> SEQUENCE: 2

Met Ser Leu Ser Thr Glu Gln Met Leu Arg Asp Tyr Pro Arg Ser Met
1               5                   10                  15

Gln Ile Asn Gly Gln Ile Pro Lys Asn Ala Ile His Glu Thr Tyr Gly
            20                  25                  30

Asn Asp Gly Val Asp Val Phe Ile Ala Gly Ser Gly Pro Ile Gly Ala
        35                  40                  45

Thr Tyr Ala Lys Leu Cys Val Glu Ala Gly Leu Arg Val Val Met Val
    50                  55                  60

Glu Ile Gly Ala Ala Asp Ser Phe Tyr Ala Val Asn Ala Glu Glu Gly
65                  70                  75                  80

Thr Ala Val Pro Tyr Val Pro Gly Tyr His Lys Lys Asn Glu Ile Glu
                85                  90                  95

Phe Gln Lys Asp Ile Asp Arg Phe Val Asn Val Ile Lys Gly Ala Leu
            100                 105                 110

Gln Gln Val Ser Val Pro Val Arg Asn Gln Asn Val Pro Thr Leu Asp
        115                 120                 125

Pro Gly Ala Trp Ser Ala Pro Pro Gly Ser Ser Ala Ile Ser Asn Gly
    130                 135                 140

Lys Asn Pro His Gln Arg Glu Phe Glu Asn Leu Ser Ala Glu Ala Val
145                 150                 155                 160

Thr Arg Gly Val Gly Gly Met Ser Thr His Trp Thr Cys Ser Thr Pro
                165                 170                 175

Arg Ile His Pro Pro Met Glu Ser Leu Pro Gly Ile Gly Arg Pro Lys
            180                 185                 190

Leu Ser Asn Asp Pro Ala Glu Asp Lys Glu Trp Asn Glu Leu Tyr
        195                 200                 205

Ser Glu Ala Glu Arg Leu Ile Gly Thr Ser Thr Lys Glu Phe Asp Glu
    210                 215                 220
```

```
Ser Ile Arg His Thr Leu Val Leu Arg Ser Leu Gln Asp Ala Tyr Lys
225                 230                 235                 240

Asp Arg Gln Arg Ile Phe Arg Pro Leu Pro Leu Ala Cys His Arg Leu
            245                 250                 255

Lys Asn Ala Pro Glu Tyr Val Glu Trp His Ser Ala Glu Asn Leu Phe
            260                 265                 270

His Ser Ile Tyr Asn Asp Asp Lys Gln Lys Leu Phe Thr Leu Leu
        275                 280                 285

Thr Asn His Arg Cys Thr Arg Leu Ala Leu Thr Gly Gly Tyr Glu Lys
    290                 295                 300

Lys Ile Gly Ala Ala Glu Val Arg Asn Leu Leu Ala Thr Arg Asn Pro
305                 310                 315                 320

Ser Ser Gln Leu Asp Ser Tyr Ile Met Ala Lys Val Tyr Val Leu Ala
                325                 330                 335

Ser Gly Ala Ile Gly Asn Pro Gln Ile Leu Tyr Asn Ser Gly Phe Ser
            340                 345                 350

Gly Leu Gln Val Thr Pro Arg Asn Asp Ser Leu Ile Pro Asn Leu Gly
        355                 360                 365

Arg Tyr Ile Thr Glu Gln Pro Met Ala Phe Cys Gln Ile Val Leu Arg
    370                 375                 380

Gln Glu Phe Val Asp Ser Val Arg Asp Pro Tyr Gly Leu Pro Trp
385                 390                 395                 400

Trp Lys Glu Ala Val Ala Gln His Ile Ala Lys Asn Pro Thr Asp Ala
                405                 410                 415

Leu Pro Ile Pro Phe Arg Asp Pro Glu Pro Gln Val Thr Thr Pro Phe
            420                 425                 430

Thr Glu Glu His Pro Trp His Thr Gln Ile His Arg Asp Ala Phe Ser
        435                 440                 445

Tyr Gly Ala Val Gly Pro Glu Val Asp Ser Arg Val Ile Val Asp Leu
    450                 455                 460

Arg Trp Phe Gly Ala Thr Asp Pro Glu Ala Asn Asn Leu Leu Val Phe
465                 470                 475                 480

Gln Asn Asp Val Gln Asp Gly Tyr Ser Met Pro Gln Pro Thr Phe Arg
                485                 490                 495

Tyr Arg Pro Ser Thr Ala Ser Asn Val Arg Ala Arg Lys Met Met Ala
            500                 505                 510

Asp Met Cys Glu Val Ala Ser Asn Leu Gly Gly Tyr Leu Pro Thr Ser
        515                 520                 525

Pro Pro Gln Phe Met Asp Pro Gly Leu Ala Leu His Leu Ala Gly Thr
    530                 535                 540

Thr Arg Ile Gly Phe Asp Lys Ala Thr Thr Val Ala Asp Asn Asn Ser
545                 550                 555                 560

Leu Val Trp Asp Phe Ala Asn Leu Tyr Val Ala Gly Asn Gly Thr Ile
                565                 570                 575

Arg Thr Gly Phe Gly Glu Asn Pro Thr Leu Thr Ser Met Cys His Ala
            580                 585                 590

Ile Lys Ser Ala Arg Ser Ile Ile Asn Thr Leu Lys Gly Gly Thr Asp
        595                 600                 605

Gly Lys Asn Thr Gly Glu His Arg Asn Leu
    610                 615

<210> SEQ ID NO 3
<211> LENGTH: 30
<212> TYPE: PRT
```

```
<213> ORGANISM: Lyophyllum shimeji

<400> SEQUENCE: 3

Asn Ala Glu Glu Gly Thr Ala Val Pro Tyr Val Pro Gly Tyr His Lys
1               5                   10                  15

Lys Asn Glu Ile Glu Phe Gln Lys Asp Ile Asp Arg Phe Val
            20                  25                  30

<210> SEQ ID NO 4
<211> LENGTH: 24
<212> TYPE: PRT
<213> ORGANISM: Lyophyllum shimeji

<400> SEQUENCE: 4

Glu Phe Asp Glu Ser Ile Arg His Thr Leu Val Leu Arg Ser Leu Gln
1               5                   10                  15

Asp Ala Tyr Lys Asp Arg Gln Arg
            20

<210> SEQ ID NO 5
<211> LENGTH: 29
<212> TYPE: PRT
<213> ORGANISM: Lyophyllum shimeji

<400> SEQUENCE: 5

Ala Glu Arg Leu Ile Gly Thr Ser Thr Lys Glu Phe Asp Glu Ser Ile
1               5                   10                  15

Arg His Thr Leu Val Leu Arg Ser Leu Gln Asp Ala Tyr
            20                  25

<210> SEQ ID NO 6
<211> LENGTH: 34
<212> TYPE: PRT
<213> ORGANISM: Lyophyllum shimeji

<400> SEQUENCE: 6

Ala Glu Arg Leu Ile Gly Thr Ser Thr Lys Glu Phe Asp Glu Ser Ile
1               5                   10                  15

Arg His Thr Leu Val Leu Arg Ser Leu Gln Asp Ala Tyr Lys Asp Arg
            20                  25                  30

Gln Arg

<210> SEQ ID NO 7
<211> LENGTH: 20
<212> TYPE: DNA
<213> ORGANISM: Artificial Sequence
<220> FEATURE:
<223> OTHER INFORMATION: Derived from Lyophyllum shimeji
<221> NAME/KEY: misc_feature
<222> LOCATION: (1)..(20)
<223> OTHER INFORMATION: n represents inosine

<400> SEQUENCE: 7
gargarggna cngcngtncc                                              20

<210> SEQ ID NO 8
<211> LENGTH: 23
<212> TYPE: DNA
<213> ORGANISM: Artificial Sequence
<220> FEATURE:
<223> OTHER INFORMATION: Derived from Lyophyllum shimeji

<400> SEQUENCE: 8
```

```
garttycara argayathga ymg                                              23

<210> SEQ ID NO 9
<211> LENGTH: 23
<212> TYPE: DNA
<213> ORGANISM: Artificial Sequence
<220> FEATURE:
<223> OTHER INFORMATION: Derived from Lyophyllum shimeji
<221> NAME/KEY: misc_feature
<222> LOCATION: (1)..(23)
<223> OTHER INFORMATION: n represents inosine

<400> SEQUENCE: 9
ttygtnaayg tnathtgygg ngc                                              23

<210> SEQ ID NO 10
<211> LENGTH: 23
<212> TYPE: DNA
<213> ORGANISM: Artificial Sequence
<220> FEATURE:
<223> OTHER INFORMATION: Derived from Lyophyllum shimeji
<221> NAME/KEY: misc_feature
<222> LOCATION: (1)..(23)
<223> OTHER INFORMATION: n represents inosine

<400> SEQUENCE: 10
tgnckdatns wytcrtcraa ytc                                              23

<210> SEQ ID NO 11
<211> LENGTH: 23
<212> TYPE: DNA
<213> ORGANISM: Artificial Sequence
<220> FEATURE:
<223> OTHER INFORMATION: Derived from Lyophyllum shimeji
<221> NAME/KEY: misc_feature
<222> LOCATION: (1)..(23)
<223> OTHER INFORMATION: n represents inosine

<400> SEQUENCE: 11
tgnckrtcyt trtangcrtc ytg                                              23

<210> SEQ ID NO 12
<211> LENGTH: 23
<212> TYPE: DNA
<213> ORGANISM: Artificial Sequence
<220> FEATURE:
<223> OTHER INFORMATION: Derived from Lyophyllum shimeji
<221> NAME/KEY: misc_feature
<222> LOCATION: (1)..(23)
<223> OTHER INFORMATION: n represents inosine

<400> SEQUENCE: 12
ggngcraada tnckytgnck rtc                                              23
```

US 6,881,720 B1

ANTIMICROBIAL PROTEIN FROM LYOPHYLLUM SHIMEJI

This application is the national phase under 35 U.S.C. § 371 of PCT International Application No. PCT/JP00/06404 which has an International filing date of Sep. 20, 2000, which designated the United States of America and was not published in English.

TECHNICAL FIELD

This invention relates to a novel protein having an antimicrobial activity, a gene encoding the protein, and a method of using the protein and the gene. More particularly, it relates to a protein originated from *Lyophyllum shimeji*, and having an antimicrobial activity at least against *Rhizoctonia solani* and *Pyricularia oryzae*, a gene encoding the protein, and a method of using the protein and the gene.

The present application claims priority based on Japanese Patent Application No. 267238/1999 filed on Sep. 21, 1999, the entire contents of which are incorporated herein as a reference.

BACKGROUND ART

Lytic enzymes such as chitinase and $\beta$-1,3-glucanase are known as plant proteins having antifungal or antimicrobial activity against plant pathogenic microorganisms. In vitro experiments have shown that while these types of enzymes will exert their effect if employed alone (Schlumbaum et al. (1986), Nature 324, pp. 365–367; Broglie et al. (1991), Science 254, pp. 1194–1197), if a combination of two or more such enzymes is employed, an enhanced effect can generally be obtained (Mauch et al. (1988), Plant Physiol. 88, pp. 936–942; Sela-Buurlage et al. (1993), Plant Physlol. 101, pp. 857–863). If used to inhibit fungal growth, it is known that these lytic enzymes are required to be used at a concentration of from about several ten to several hundred μg/ml when used alone, or about several μg/ml per enzyme when used in combination. However, so far as the present inventors are aware, none of these lytic enzymes has been demonstrated to exert any antimicrobial effect against *Pyricularia oryzae* which causes extensive damage to rice crops.

Antifungal peptides (AFP) of low molecular weight exemplified by defensin, also have antimicrobial activity and, among them, it is reported that Ca-AMP1 (Japanese domestic announcement No. 505048/96) and CB-1 (Oita et al. (1996), Biosci. Biotech. Biochem. 60, pp. 481–483) show antimicrobial activity against both *Pyricularia oryzae* and *Rhizoctonia solani*. While Rs-AFP1 and Ar-AFP2 (Terras et al. 1992, J. Biol. Chem. 267, pp. 15301–15309), and Ace-AMP1 (Japanese domestic announcement No. 501424/97) show antimicrobial activity against *Pyricularia oryzae*. These low-molecular weight peptides inhibit 50% of the growth of plant pathogenic microorganisms including the ones mentioned above at a concentration of several μg/ml.

Also, attempts have been made to isolate lytic enzyme genes or low-molecular weight antimicrobial peptide genes and transfer these genes into plants to thereby construct plants tolerant to injury from disease (Broglie et al. (1991), Science 254, pp. 1194–1197; Zhu et al. (1994), Bio/Technology 12, pp. 807–812; Lin et al. (1995), Bio/Technology 13, pp. 686–691; Terras et al. (1995). The Plant Cell 7, pp. 573–588). However hardly any plants to which tolerance at a practically acceptable level is imparted have hitherto been obtained. One reason for this is considered to be that the transferred genes are expressed at a low level only. However, a more fundamental reason is considered to be that antimicrobial proteins per se reported so far have poor antimicrobial activity. Consequently, it has been desired to identify and utilize an antimicrobial protein which is superior in antimicrobial activity to those of the prior art.

SUMMARY OF THE INVENTION

An object of the present invention is to screen and identify a novel antimicrobial protein capable of inhibiting the growth of various plant pathogenic microorganisms including *Pyricularia oryzae* and *Rhizoctonia solani*, which are causative of two major diseases which affect rice, even at relatively low concentrations.

Another object of the present invention is to clone a gene encoding the novel protein and to determine the base sequence thereof.

Still another object of the present invention is to introduce the gene according to the present invention into, a host organism (a microorganism, an animal, a plant, etc.) to construct a transformant, thereby using the gene of the present invention.

Still another object of the present invention is to provide an antimicrobial agent containing the antimicrobial protein according to the present invention.

DETAILED DESCRIPTION OF THE INVENTION

Figure 1:
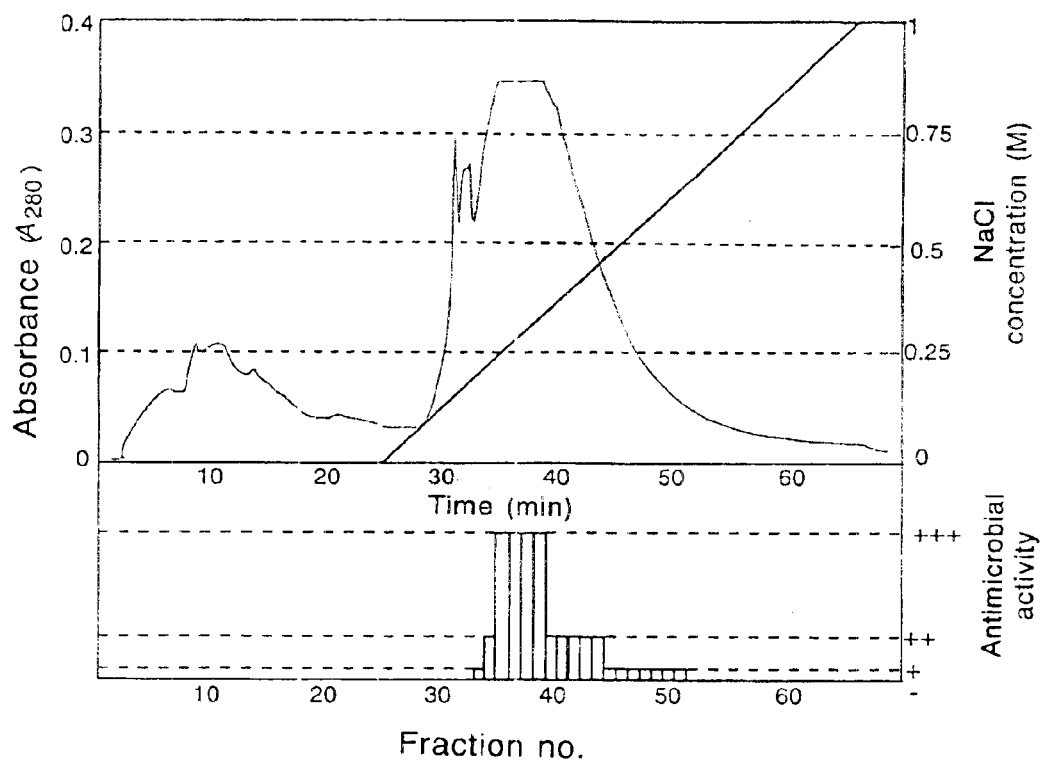
FIG. 1 shows the relationship between the separation chart of *Lyophyllum shimeji* proteins by using a MonoQ column and the antimicrobial activity thereof.
Figure 2:
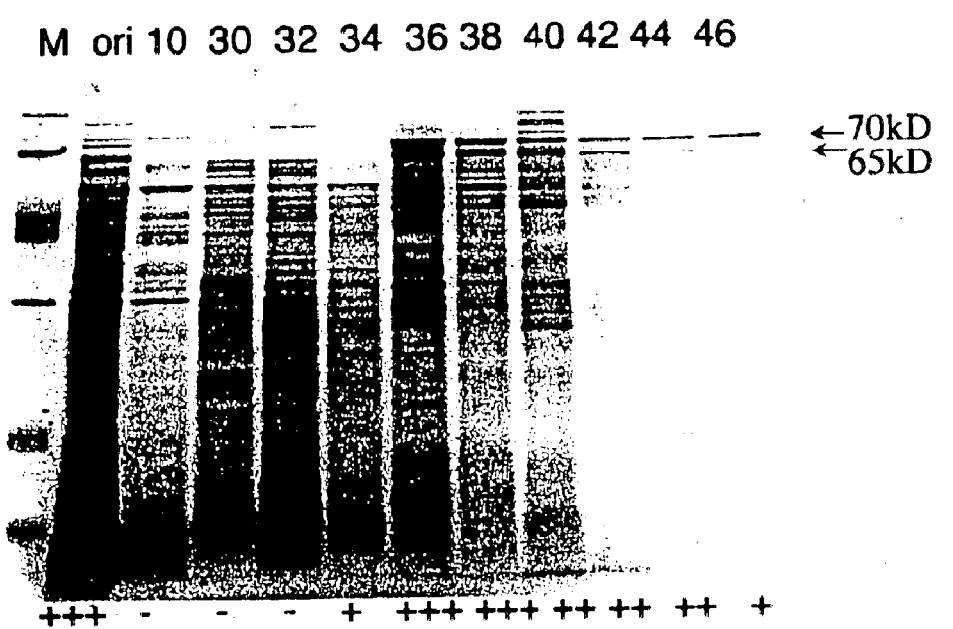
FIG. 2 shows the relationship between the electrophoretic pattern of *Lyophyllum shimeji* proteins separated by a MonoQ column, and the antimicrobial activity thereof. The numbers given above the lanes correspond respectively to the fraction numbers in FIG. 1, while M indicates molecular weight markers. The symbols (−, +, ++, +++) given below the lanes indicate the antimicrobial activity strength. The arrows show antimicrobial proteins (70 kDa and 65 kDa).

As a result of intensive study of the above problems, the present inventors have established an assay system for determining antimicrobial activity against *Pyricularia oryzae* and *Rhizoctonia solani* in vitro. Having achieved this, they extracted proteins from an edible mushroom *Lyophyllum shlmeji*. The extracted proteins were then subjected to a combination of an ion exchange column chromatography and a high performance liquid chromatography (HPLC) and each fraction thus obtained was examined by using the assay system. Thus, the inventors successively identified, isolated and purified an antimicrobial protein. Further, partial amino acid sequences of the purified protein were determined. The RT-PCR was then performed using oligonucleotides synthesized on the basis of these amino acid sequences as primers, thereby obtaining a partial length cDNA encoding the protein. Subsequently, a cDNA library originated from *Lyophyllum shimeji* was screened by using this partial length cDNA as a probe. As a result, a full-length cDNA encoding the above-described protein was isolated and the full base sequence thereof was determined. Thus, the present inventors have successfully isolated a novel antimicrobial protein originated from *Lyophyllum shimeji* and cloned a DNA encoding the protein. Moreover, they determined the amino acid sequence of the protein and the base sequence of the DNA, thereby completing the present invention.

According to the first aspect, therefore, the present invention provides an antimicrobial protein which can be obtained from a fraction of an aqueous extract of *Lyophyllum shimeji* precipitated by the ammonium sulfate precipitation method, and the protein has been demonstrated to have an antimicrobial activity at least against *Rhizoctonia solani* or *Pyricularia oryzae*, and has a molecular weight of about 70 kDa as a precursor type and a molecular weight of about 65 kDa as a mature type using the SDS-PAGE method.

Typically, the antimicrobial protein according to the present invention has an amino acid sequence of SEQ ID NO:2 in the Sequence Listing. It is presumed that the mature type of about 65 kDa consists of the amino acid residues 76 to 618 in SEQ ID NO:1, though the present invention is not restricted thereto.

The antimicrobial protein according to the present invention involves not only the antimicrobial protein having the amino acid sequence of SEQ ID NO:2, but also antimicrobial proteins having an amino acid sequence having one or more amino acid mutations therein, or an amino acid sequence having a 50% or more homology with this sequence and showing an antimicrobial activity against *Rhizoctonia solani* or *Pyricularia oryzae*.

Preferably, the antimicrobial protein according to the present invention has a 60% or more, still preferably 70% or more, still preferably 80% or more, particularly preferably 90% or more and most preferably 95% or more, homology with the amino acid sequence of SEQ ID NO:2 in the Sequence Listing.

According to the second aspect, the present invention provides an antimicrobial protein comprising a single polypeptide selected from among a polypeptide having the partial amino acid sequence of, for example, the amino acid residues 76 to 618 in the amino acid sequence of SEQ ID NO:2 in the Sequence Listing; a polypeptide having an amino acid sequence having one or more amino acid mutations therein, and a polypeptide having an amino acid sequence having a 50% or more homology with this sequence and showing an antimicrobial activity against *Rhizoctonia solani* or *Pyricularia oryzae*, or a combination of these polypeptides.

As regards the above-described antimicrobial protein according to the second aspect of the present invention, the definition "protein having a 50% or more homology" with each particular amino acid sequence means that it is acceptable so long as it has at least 50% homology. However, it is intended that this protein has an amino acid sequence preferably having a 60% or more, still preferably 70% or more, still preferably 80% or more, particularly preferably 90% or more and most preferably 95% or more, homology.

According to the third aspect, the present invention provides a process for producing an antimicrobial protein of the present invention comprising:

a step of recovering fraction(s) of an aqueous extract of *Lyophyllum shimeji* precipitated by the ammonium sulfate precipitation method with 75%-saturataion of ammonium sulfate; and a step of subjecting the fraction(s) to ion exchange chromatography and recovering fraction(s) eluted at NaCl concentration of 0.05 M to 1 M.

According to the fourth aspect, the present invention provides a gene encoding the antimicrobial protein of the present invention.

Typically, the gene according to the present invention has a base sequence of SEQ ID NO:1 in the Sequence Listing, a base sequence derived from this base sequence by substitution, deletion, insertion and/or addition of one or more bases, or a base sequence capable of hybridizing to the above-described base sequence(s) under stringent conditions.

The gene according to the present invention has a base sequence generally having a 50% or more, preferably 60% or more, still preferably 70% or more, still preferably 80% or more, particularly preferably 90% or more and most preferably 95% or more, homology with the base sequence of SEQ ID NO:1 in the Sequence Listing.

According to the fifth aspect, the present invention provides an oligonucleotide for obtaining a gene encoding an antimicrobial protein originated from *Lyophyllum shimeji* produced by a process comprising:

selecting two domains satisfying the following requirements from the base sequence of the gene encoding the antimicrobial protein of SEQ ID NO:1 in the Sequence Listing:

1) each domain consisting of 15 to 30 bases; and
2) each domain having 40 to 60% of G+C;

preparing single-stranded DNAs having base sequences which are identical to the base sequences of said domains or complementary thereto, or preparing a single-stranded DNA mixture having degeneracy in the genetic code which ensures that the amino acid residues coded by the single-stranded DNAs are not changed; and optionally modifying the single-stranded DNAs while avoiding damage to the binding specificity to the base sequence of the gene encoding the antimicrobial protein.

Preferably, the oligonucleotide according to the present invention has a nucleotide sequence of any of SEQ ID NOS:7 to 12 in the Sequence Listing.

According to the sixth aspect, the present invention provides a method of isolating the gene according to the present invention, wherein the method comprises effecting a nucleic acid amplification reaction using a *Lyophyllum shimeji* cDNA library as a template, and a pair of two oligonucleotides described above as primers to thereby amplify a part of the gene encoding the antimicrobial protein of the present invention, and screening the cDNA library using the amplification product thus obtained as a probe to thereby isolate full-length cDNA clones.

According to the seventh aspect, the present invention provides a recombinant vector containing the gene of the present invention.

As for the recombinant vector of the present invention, it is preferable that the vector is an expression vector.

According to the eighth aspect, the present invention provides a transformant obtained by introducing the recombinant vector of the present invention into a host organism.

According to the ninth aspect, the present invention provides an antimicrobial agent comprising the antimicrobial protein according to the present invention as the active ingredient.

Now, preferred embodiments will be described in detail to illustrate the present invention.

According to the first aspect of the present invention, a protein originated from *Lyophyllum shimeji* having an antimicrobial activity against plant pathogenic microorganisms, is provided. The present protein is not restricted in origin, production process or the like, so long as it has the characteristics stated in this specification. Namely, the antimicrobial protein of the present invention may be either a natural protein, a protein expressed from a recombinant DNA with the use of genetic engineering techniques, or a chemically synthesized protein.

Typically, the protein according to the present invention has an amino acid sequence consisting of 618 amino acids as of SEQ ID NO:2 in the Sequence Listing. However, it is well known that natural proteins are accompanied by mutant proteins having one or more amino acid mutations caused by differences in varieties of the organisms producing the protein, gene mutations depending on difference in ecotype or the presence of closely similar isozymes. The term "amino acid mutation" as used herein means the substitution, deletion, insertion and/or addition, etc. of one or more amino acids. Although the protein according to the present invention has an amino acid sequence of SEQ ID NO:2 deduced from the base sequence of the cloned gene, it is not restricted to the protein having this sequence. Namely, it is intended that homologous proteins be included in the present invention so long as they have the characteristics stated in this specification. The homology is at least 50% or more, preferably 60% or more, still preferably 70% or more, still preferably 80% or more, particularly preferably 90% or more and most preferably 95% or more.

In this specification, the homology percentage can be determined by comparing the sequence data by using, for example, a BLAST program reported by Altschul et al. (Nucl. Acids. Res. 25, pp. 3389–3402, 1997). This program is available on the Internet from the Internet Web Site of National Center for Biotechnology Information (NCBI) or DNA Data Bank of Japan (DDBJ). Various conditions (parameters) for searching the homology by the BLAST program are stated in detail in this site. Although the configuration may be somewhat modified, searches can be performed usually by using the defaults.

In general, a mutant obtained by substituting one or more amino acid residue(s) by other one or more amino acid residue(s) having similar properties (for example, substitution of a hydrophobic amino acid by another hydrophobic amino acid, substitution of a hydrophilic amino acid by another hydrophilic amino acid, substitution of an acidic amino acid by another acidic amino acid, or substitution of a basic amino acid by another basic amino acid) has properties similar to the intact protein. Procedures for preparing recombinant proteins having such a desired mutation by using genetic engineering techniques are well known to those skilled in the art, and therefore, these mutant proteins also fall within the scope of the present invention.

The protein of the present invention has a molecular weight of about 70 kDa as the precursor type, which corresponds to the polypeptide having an amino acid sequence of 1 to 618 in SEQ ID NO:2 in the Sequence Listing, and a molecular weight of about 65 kDa as the mature type, which corresponds to the polypeptide having an amino acid sequence of 76 to 618 in SEQ ID NO:2 in the Sequence Listing, in the SDS-PAGE method. Typically, the antimicrobial protein according to the present invention has the amino acid sequence of SEQ ID NO:2 in the Sequence Listing, though it is not restricted thereto.

Accordingly, the present invention provides an antimicrobial protein comprising a single polypeptide selected from among a polypeptide having the partial amino acid sequence of 1 to 618 in the amino acid sequence of SEQ ID NO:2 in the Sequence Listing; and a polypeptide having the amino acid sequence of 76 to 618, or a combination of the same. The above-described polypeptides include homologous polypeptides having mutations as described above in the specification.

The protein according to the present invention can be purified from *Lyophyllum shimeji* fruit body by using the ammonium sulfate precipitation method, ion exchange column chromatography, etc. as will be described in Examples which follow. Alternatively, a corresponding protein can be obtained in a large amount by introducing the DNA sequence of 8 to 1861 or the DNA sequence of 233 to 1861 in SEQ ID NO:1 in the Sequence Listing according to the present invention into *E. coli*, a yeast, an insect or a specific animal cell by using an expression vector capable of amplifying in the host and expressing the protein.

As result of homology searching of the *Lyophyllum shimeji*-origin protein according to the present invention by using the BLAST program of DDBJ, it is revealed that a homology of 45% is observed between full-length amino acid sequences even in the highest case and no other homologous sequence have been found. Based on these facts, it is concluded that this protein is a novel protein. As a result of the disclosure in the present invention of the amino acid sequence of this protein and the DNA sequence coding therefor, genes encoding proteins having similar physiological activity can be easily isolated from other organism species by using genetic engineering techniques (hybridization, nucleic acid amplification such as PCR, etc.) with the use of these sequences or a portion thereof. In such a case, novel proteins coded by these genes also fall within the scope of the present invention. As a result of the homology searching on the DNA sequence according to the present invention, only one sequence within an extremely short length (32 bases) hits with a homology of 93%.

The pyranose oxidase of *Coriolus versicolor* shows the highest homology (45% between the full amino acid sequences) with the *Lyophyllum shimeji*-origin antimicrobial protein of the present invention. The Pyranose oxidase is an enzyme which oxidizes pyranoses such as glucose to form a 2-keto product and hydrogen peroxide. It is reported that this enzyme is applicable to the assay of other pyranoses (see Japanese Patent Public Disclosure NO. 205861/96 incorporated herein as a reference). It was found that the *Lyophyllum shimeji*-origin antimicrobial protein according to the present invention actually shows pyranose oxidase activity, and its specific activity is extremely high while Km values to glucose and the like are low. The strength of the antimicrobial activity in the ion exchange column fraction is as would be expected from the strength of the pyranose oxidase activity. It is therefore estimated that the antimicrobial activity of the *Lyophyllum shimeji*-origin antimicrobial protein found in the present invention relates to pyranose oxidase. In terms of the functional mechanism of the antimicrobial activity of the present invention, one theory is that hydrogen peroxide formed by this enzyme in the course of the oxidation of glucose contained in an assay medium, exerts harmful effects on pathogenic microorganisms, although it is not intended to stick to this theory.

The protein according to the present invention can be purified and isolated by appropriately combining procedures commonly employed in the purification and isolation of proteins such as ammonium sulfate precipitation, ion exchange chromatography (MonoQ, A Sepharose, DEAE, etc.) and the like.

As in Examples given hereinafter, for example, *Lyophyllum shimeji* is grained and extracted with a buffer. After filtering the extract, ammonium sulfate is added to the supernatant to give an appropriate concentration (for example, 75%-saturation) and the mixture is allowed to stand. Thus a precipitate containing the protein according to the present invention can be obtained. The precipitate is dialyzed and subjected to ion exchange chromatography to eluate with a salt concentration gradient (for example, 50 mM to 1 M of sodium chloride), thereby recovering a fraction containing the desired protein.

The present invention further provides a gene encoding the antimicrobial protein of the present invention. Types of gene are not restricted. Namely, it may be either a DNA from a natural origin, a recombinant DNA, a chemically synthesized DNA. The gene may be a genomic cDNA or a cDNA clone.

Typically, the gene of the present invention has the base sequence of SEQ ID NO:1 in the Sequence Listing. However, SEQ ID NO:1 is the base sequence of a clone obtained in the following Example which is merely an example of the present invention. It is well known to a person skilled in the art that natural genes are accompanied by a small number of mutations caused by difference in varieties of the organism producing the same, or difference in ecotype, or a small number of mutations caused by the presence of closely similar isozymes. Accordingly, the gene of the present invention is not restricted to the gene having a base sequence of SEQ ID NO:1 in the Sequence Listing but can include any genes encoding the antimicrobial protein of the present invention.

As a result of the disclosure in the present invention of the amino acid sequence of this protein and the DNA sequence coding therefor, genes encoding proteins having similar physiological activity can easily be isolated from other organism species by using genetic engineering techniques (hybridization, nucleic acid amplification, etc.) with the use of these sequences or a part thereof. In such a case, the resultant genes also fall within the scope of the present invention.

Screening of a homologous gene may be carried out under arbitrary conditions without any restriction. In general, it is preferable to employ stringent conditions (for example, 6×SSC, 5× Denhardt's, 0.1% SDS, 25° C. to 68° C.). The hybridization temperature preferably ranges from 45° C. to 68° C. (without formamide) or 25° C. to 50° C. (with 50% formamide). It is well known to a person skilled in the art that DNAs comprising nucleotide sequences having a homology of a certain level or above can be cloned by appropriately setting hybridization conditions (formamide concentration, salt concentration, temperature, etc.). Homologous genes thus cloned are all included in the scope of the present invention.

Examples of the nucleic acid amplification reactions include reactions which are carried out utilizing temperature circulation such as polymerase chain reaction (PCR) (Saiki et al., 1985, Science 230, pp. 1350–1354), ligase chain reaction (LCR) (Woh et al., 1989, Genomics 4, pp. 560–569; Baringer et al., 1990, Gene 89, pp. 117–122; and Baranny et al., 1991, Proc. Natl. Acad. Sci USA 88, pp. 189–193) and amplification based on transcription (Kwoh et al., 1989, Proc. Natl. Acad. Sci. USA 86, pp. 1173–1177) and isothermal reactions such as strand displacement amplification (SDA) (Walker et al., 1992, Proc. Natl. Acad. Sci. USA 89, pp. 392–396; and Walker et al., 1992, Nuc. Acids. Res. 20, pp. 1691–1696), self-sustained sequence replication (3SR) (Guatelli et al., 1990, Proc. Natl. Acad. Sci USA 87, pp. 1874–1878) and Qβ replicase system (Lizardi et al., 1988, BioTechnology 6, pp. 1197–1202). Moreover, use can be made of a nucleic acid sequence based amplification (NASBA) on the basis of competitive amplification of a target nucleic acid and a mutant sequence as reported in European Patent No. 0525882 and the like. It is preferable to use the PCR method therefor.

Such a homologous gene cloned by using the above-described hybridization, nucleic acid amplification, etc. has a homology of at least a 50%, preferably 60% or more, still preferably 70% or more, still preferably 80% or more, particularly preferably 90% or more and most preferably 95% or more, with the base sequence of SEQ ID NO:1 in the Sequence Listing.

The present invention further provides an oligonucleotide for obtaining an antimicrobial protein originating in *Lyophyllum shimeji* produced by a process comprising:

selecting two domains satisfying the following requirements from the base sequence of the gene encoding the antimicrobial protein of SEQ ID NO:1 in the Sequence Listing:

1) each domain consisting of 15 to 30 bases; and
2) each domain having 40 to 60% of G+C;

preparing single-stranded DNAs having base sequences which are identical to the base sequences of these domains or complementary thereto, or preparing a single-stranded DNA mixture having degeneracy in the genetic code which ensures that the amino acid residues coded by the single-stranded DNAs are not changed; and optionally modifying the single-stranded DNAs while avoiding damage to the binding specificity to the base sequence of the gene encoding the antimicrobial protein. The oligonucleotides according to the present invention can be used in hybridization for detecting or isolating the gene of the present invention. It is also possible to use an appropriate pair of these oligonucleotides as primers in amplification reactions such as PCR.

The oligonucleotides according to the present invention may have nucleotide sequences of any of SEQ ID NOs:8 to 12 in the Sequence Listing. These nucleotide sequences are designed as PCR primers for cloning gene fragments encoding respective proteins. These primers comprise all of potential bases encoding the corresponding amino acids mixed together.

A fragment of the gene according to the present invention can be amplified and isolated by carrying out a nucleic acid amplification reaction (PCR, etc.) by using a *Lyophyllum shimeji* fruit body cDNA library as a template and an appropriate combination of the above oligonucleotides. Full length cDNA clones can be isolated by further screening the cDNA library by using the thus obtained amplification product as a probe by, for example, plaque hybridization. The procedures and conditions for the nucleic acid amplification reaction, the plaque hybridization conditions and others are well known to a person skilled in the art.

The present invention further provides a recombinant vector containing the gene according to the present invention. A DNA fragment of the gene of the present invention may be integrated into a vector such as a plasmid in accordance with, for example, the method reported by Sambrook, J. et al. (Molecular Cloning, A Laboratory Manual (2nd edition). Cold Spring Harbor Laboratory, 1.53 (1989)). More conveniently, use can be made of a commercially available ligation kit (for example, a product by Takara Shuzo Co., Ltd.). The recombinant vector (for example, a recombinant plasmid) thus obtained is transferred into a host cell (for example, *E-coli* TB1, LE392 or XL-1Blue).

Examples of the methods for transferring a plasmid into the host cells include the calcium phosphate method, the calcium chloride/rubidium chloride method, the electroporation method, the electorinjeciton method, treatment with a chemical such as PEG and the like, and the method using a gene shotgun, as reported by Sambrook, J. et al., Molecular Cloning, A Laboratory Manual (2nd edition), Cold Spring Harbor Laboratory, 1.74 (1989), Conveniently, the vector can be prepared by ligating a desired gene to a recombinant vector available in the art (for example, a plasmid DNA). Specific examples of the vectors usable herein include plasmids originated from *E. coli*, such as pBluescript, pUC18, pUCl9 and pBR322, though the present invention is not restricted thereto.

An expression vector is particularly useful in order to produce the desired protein. The expression vector is not particularly restricted in type, so long as it has a function of expressing the desired gene in various procaryotic and/or eucaryotic host cells and thus producing the desired protein. Preferred examples of the vector include expression vectors for *E. coli*, such as, pQE-30, pQE-60, pMAL-C2, pMAL-p2, pSE420, etc. As the vector for the expression in yeasts, pYES2 (the genus of *Saccharomyces*), and pPIC3.5K, pPIC9K and pAO815 (the genus *Pichia*) are preferable. As the vector for the expression in insects, pBacPAK8/9, pBK283, pVL1392, pBlueBac4.5, etc. are preferable.

A transformant can be prepared by transferring a desired expression vector into a host cell. The host cell to be used is not particularly restricted, so long as it is compatible with the expression vector according to the present invention and can be transformed thereby. Namely, use can be made of various cells commonly employed in the art, including natural cells and artificially established recombinant cells. Examples thereof include bacteria (those belonging to the genera *Escherichia* and *Bacillus*), yeasts (those belonging to the genera *Saccharomyces. Pichia*, etc.), animal cells, insect cells and plant cells.

As the host cell, it is preferable to use *E. coli*, yeasts or insect cells. Particular examples thereof include *E. coli* strains (M15, JM109, BL21, etc.), yeasts (INVSc1 (*Saccharomyces*), GS115 and KM71 (each *Pichia*), etc.) and insect cells (BmN4, silkworm larva, etc.). Examples of animal cells include cells originating from mouse, *Xenopus*, rat, hamster, monkey, human, and cultured cell lines established from the above cells. The plant cells, not particularly restricted so long as they can be cultured, include cells originating from tobacco, *Arabidopsis*, rice, corn and wheat, for example.

In the case of using a bacterium (in particular, *E. coli*) as the host cell, an expression vector generally consists at least of a promoter/operator domain, an initiation codon, a gene encoding the desired antimicrobial protein, a termination codon, a terminator and a replicable unit.

In the case of using a yeast, a plant cell, an animal cell or an insect cell as the host cell, it is generally preferable for an expression vector to contain at least a promoter, an initiation codon, a gene encoding the desired antimicrobial protein, a termination codon and a terminator. Moreover, it may optionally contain a DNA encoding a signal peptide, an enhancer sequence, the non-translated domains in the 5' and 3' sides of a desired gene, a selection marker domain, a replicable unit and the like.

An appropriate example of the initiation codon in the vector according to the present invention is a methionine codon (ATG). Examples of the termination codon include those commonly employed ones such as TAG, TGA and TAA.

The term "replicable unit" as used herein means a DNA capable of replicating its entire DNA sequence in a host cell. Examples thereof include natural plasmids, artificially modified plasmids (i.e. plasmids prepared from natural plasmids) and synthetic plasmids. Appropriate examples of the plasmid include plasmids pQE30, pET, pCAL or artificially modifications thereof (e.g. DNA fragments obtained by treating pQE30, pET or PCAL with adequate restriction enzyme(s) in case of *E. coli*; plasmid pYES2 and pPIC9K in case of yeasts; and a plasmid pBacPAK8/9, etc. in the case of insect cells.

As the enhancer sequence and the terminator sequence, use may be made of those commonly employed by a person skilled in the art, for example, sequences originating from SV40.

As the selection marker, use may be made of those commonly employed in the art by using a conventional method. Examples thereof include antibiotic resistance genes (*tetracycline, ampicillin, kanamycin, neomycin, hygromycin, spectinomycin*, etc.).

The expression vector can be prepared by ligating at least the above-described promoter, the initiation codon, the gene encoding the desired antimicrobial protein, the termination codon and the terminator domain, consecutively and cyclically to an appropriate replicable unit. In this process, it is also possible to use appropriate DNA fragment(s) (for example, linker, other restriction enzyme sites, etc.) by a conventional method such as digestion with restriction enzyme(s) or ligation with the use of T4DNA ligase, if desired.

The expression vector according to the present invention can be introduced (i.e., transformation (transduction)) into a host cell by using publicly known methods.

Namely, the transformation can be carried out by, for example, a method reported by Cohen et al. (Proc. Natl. Acad. Sci. USA, 69, 2110 (1972)), the protoplast method (Mol. Gen. Genet., 168, 111 (1979)) or the competent method (J. Mol. Biol., 56, 209 (1971)) in case of bacteria (*E. coli, Bacillus subtilis*, etc.); a method reported by Hinnens et al. (Proc. Natl. Acd. Sci. USA, 75, 1927 (1978)) and the lithium method (J. Bacteriol., 153, 163 (1988)) in case of *Saccharomyces cerevisiae*; the leaf disc method (Science, 227, 129 (1985)) and the electroporation method (Nature, 319, 791 (1986)) in case of plant cells; a method reported by Graham (Virology, 52, 456 (1973)) in the case of animal cells; and a method reported by Summers et al. (Mol. Cell. Biol., 3, pp. 2156–2165 (1983)) in the case of insect cells.

A vector for transforming plants is useful in constructing a plant having tolerance to diseases by using the DNA fragment according to the present invention. The vector for plants is not particularly restricted, so long as it is capable of expressing the corresponding gene and thus producing the desired protein. Examples thereof include pBI1221 and pBI121 (Clontech, Co., Ltd.) and vectors derived therefrom. Further, especially in order to transform monocotyledons, pIG121Hm, pTOK233 (Hiei et al., Plant J., 6, pp. 271–282 (1994)), pSB424 (Komari et. al, Plant J., 10, pp. 165–174 (1996)), etc. can be used, for example.

A transgenic plant can be prepared by constructing a vector for transforming plants by replacing the β-glucuronidase (GUS) gene site in the above vector with the DNA fragment according the present invention, and then transferring the vector into a plant. Preferably, the vector for transforming plants contains at least a promoter, an initiation codon, the desired gene (the DNA sequence of the present invention or a part thereof), a termination codon and a terminator. Moreover, it may optionally contain a DNA encoding a signal peptide, an enhancer sequence, the non-translated domains in 5' and 3' sides of the desired gene, a selection marker domain and the like.

The promoter and the terminator are not particularly restricted, so long as being capable of exerting the functions in plant cells. Examples of a promoter which enables constitutive expression include the 35S promoter having been integrated into the above-described vector, as well as actin and ubiquitin gene promoters. However, more preferably, an inducible promoter may be integrated. By using inducible promoter, the desired protein is produced only after the transgenic plant comes into contact with pests and thus the plant acquires tolerance. Examples of the inducible promoter usable therefor include promoters of genes of phenylalanine ammonia-lyase, chitinase, glucanase, thionine, and osmosin and other promoters of genes responding to pests or stress.

The gene transfer into plants may be carried out by a method with the use of *agrobacterium* (Horsch et al., Science, 227, 129(1985); Hiei et al., Plant J., 6, pp. 271–282 (1994)), the electroporation method (Fromm et al., Nature, 319, 791 (1986)), the PEG method (Paszkowski et al., EMBO J., 3, 2717 (1984)) the microinjection method (Crossway et al., Mol. Gen. Genet., 202, 179 (1986)), the microcollision method (McCabe et al., Bio/Technology, 6, 923 (1988)), etc. An arbitrary method may be employed therefor without restriction, so long as it is capable of transferring the gene into a desired plant. Similarly, the host plant is not restricted to a specific species, so long as it is compatible with the vector for transforming plants according to the present invention and can be transformed thereby. Namely, use can be made of plants commonly employed in the art, for example, dicotyledons (for example, tobacco, *Arabidopsis*, tomato, cucumber, carrot, soy bean, potato, beet, turnip, Chinese cabbage, rape plant, cotton, petunia, etc.) and monocotyledons (for example, rice, corn, wheat, etc.).

The antimicrobial protein according to the present invention exhibits a highly potent antimicrobial activity. For example, it completely inhibits the germination of *Pyricularia oryzae* spores at an extremely low concentration of 5 ng/ml (see Example 2 hereinafter). No germination of spores is observed after incubating at this concentration over a long period of time, which suggests that the protein of the present invention does not partially inhibit the growth of *Pyricularia oryzae*, but exerts an antimicrobial activity thereon. To the inventors' knowledge, there has been reported no antimicrobial protein hitherto which can completely inhibit the growth of pathogenic microorganisms at such a low concentration (i.e., nanogram order). In the following Examples, *Pyricularia oryzae* and *Rhizoctonia solani*, which are causative of the two major disease injuries in rice, were used in the antimicrobial assay for purifying the antimicrobial protein. However, it is a highly possible that the *Lyophyllum shimeji* antimicrobial protein identified by the present invention would exert antimicrobial effect at the comparable level on other plant diseases also. On the basis of its potent antimicrobial effect as described above, the antimicrobial protein of the present invention originated from *Lyophyllum shimeji* can be used for formulations containing the same in the active state, such as pharmaceuticals including antimicrobial agents and pesticides. When a DNA sequence encoding the protein according to the present invention is used, the protein can be produced in a large amount by integrating the DNA into an expression vector capable of functioning in *E. coli*, yeasts, etc. as described above.

The protein according to the present invention can be expressed (produced) by incubating transformant cells containing the expression vector as prepared above in a nutrient medium. The nutrient medium preferably contains carbon source(s), inorganic nitrogen source(s) or organic nitrogen source(s) required in the growth of the host cells (transformants). Examples of the carbon source include glucose, dextran, soluble starch, sucrose, methanol, etc. Examples of the inorganic nitrogen source or the organic nitrogen source include ammonium salts, nitric acid salts, amino acids, corn steep liquor, peptone, casein, meat extract, soybean cake, potato extract etc. If desired, it may further contain other nutrients such as inorganic salts (sodium chloride, potassium chloride, sodium dihydridephosphate, magnesium chloride, etc.) vitamins, and antibiotics (tetracycline, neomycin, ampicillin, kanamycin, etc.). Incubation is carried out by a method known in the art. The incubation conditions (for example, temperature, pH of the medium, incubation time) may be appropriately selected so as to produce the protein according to the present invention in a large amount. In Example 4 of the present invention, for example, the recombinant antimicrobial protein of the present invention was expressed by using *E. coli* (M15) as the host cell. In the case of the expression in *E. coli*, it is preferable that the incubation is carried out at 4° C. to 40° C. and the expression of the recombinant protein is induced by 0.01 mM to 5.0 mM of IPTG, though the present invention is not restricted thereto.

The protein according to the present invention can be recovered from the culture from the above incubation in the following manner. In the case where the protein of the present invention is accumulated in the host cells, the host cells are collected by, for example, centrifugation or filtration and then suspended in an appropriate buffer (for example, a buffer such as tris buffer, phosphate buffer, HEPES buffer or MES buffer at a concentration of about 100 mM to 10 M and with a pH value, which varies from buffer to buffer, but preferably ranges from 5.0 to 9.0). Then the cells are disrupted by a method appropriate for the host cells employed and the contents of the host cells are obtained by centrifugation. In the case where the protein of the present invention is secreted from the host cells, on the other hand, the host cells are separated from the medium by, for example, centrifugation or filtration to give a culture filtrate. The suspension of the disrupted cells or the culture filtrate may optionally be subjected to ammonium sulfate precipitation and dialyzed, and then subjected to purification and isolation of the protein of the present invention.

Purification and isolation can be carried out using the following methods. In the case where the protein is tagged with 6× histidine, GST, maltose-binding protein, or the like, use can be made of an affinity chromatography method appropriate for each tag employed. In Example 4 described hereinafter, a recombinant antimicrobial protein tagged with 6× histidine at the N-end was expressed, though the present invention is not restricted thereto. This recombinant protein was purified by using Ni-NTA agarose (manufactured by Qiagen) having an affinity for 6× histidine. In the case of producing the protein of the present invention without any tagging, on the other hand, use can be made of the ion exchange chromatography method as will be described in Examples hereinafter. It is also possible to combine these methods with gel filtration, hydrophobic chromatography, isoelectric chromatography, etc.

As discussed above, the antimicrobial protein of the present invention can be used, for example, for preventing or treating plant diseases in which fungi or bacteria are factors. Accordingly, the present invention provides an antimicrobial agent containing the antimicrobial protein of the present invention as an active ingredient. In general, the antimicrobial agent according to the present invention can be applied to whole plants or a part thereof.

The application dose varies depending on the type of plant, growth stage, conditions, application method, treating time, the type of the protein applied (for example, either the full-length protein or a protein derived therefrom by substitution, deletion, insertion and/or addition of part thereof), the weather at the growth site, the soil at the growth site and the like. It can be applied once or more a day. The application dose varies depending on various factors. It is also possible to apply the antimicrobial agent according to the present invention as a mixture with solutions, suspensions, emulsions, etc., if necessary. An aqueous or non-aqueous solution or a suspension contains one or more active substances together with at least one inert diluent. Examples of aqueous diluents include distilled water and saline. Examples of non-aqueous diluents include propylene glycol, polyethylene glycol, vegetable oils such as olive oil and alcohols such as ethanol.

These antimicrobial compositions may further contain auxiliary agents such as preservatives, humectants, emulsifiers, dispersants or stabilizers (arginine, aspartic acid, etc.).

These compositions are sterilized by, for example, filtering the composition through a bacteriostatic filer, adding a bactericide or irradiation, if necessary. It is also possible to prepare sterile solid compositions by, for example, freeze-drying and then to dissolve in distilled water or other solvents before use.

The dosage form of the antimicrobial agent thus obtained may be appropriately determined depending on the purpose. Namely, it can be mixed with the above-described additives and then applied in the form of tablets, pills, dusts, granules, solutions, emulsions, etc.

The invention will now be described in greater detail with reference to the following Examples. However it should be understood that the invention is not to be taken as being limited thereto.

EXAMPLES

Example 1

Construction of Assay System

1) Establishment of Test System

Incubation of pathogenic fungus: *Pyricularia oryzae* (TUS-1 strain, race 337, assigned from Tohoku National Agricultural Experiment Station, Ministry of Agriculture, Forestry and Fisheries) was incubated on an oatmeal medium (Difco Co. Ltd., supplemented with 1% sucrose) to give conidia. After adding 10% of glycerol, the conidium suspension was stored at −80° C.

*Rhizoctonia solani* (JT872 strain) was incubated in a 1/2 potato-dextrose broth (PD broth, Difco Co. Ltd.) for 2 days. Three hypha masses (about 5×5 mm) were lightly ground together with the 1/2 PD medium by using a Teflon homogenizer, and the fractionated hyphae thus obtained were employed as an inoculation source.

The inoculation sources as described above were added respectively to 96-well microtiter plates (Corning Co. Ltd.). The *Pyricularia oryzae* conidia were added at a density of about 1,000 per well, while the fractionated *Rhizoctonia solani* hyphae were added at a density of about 300 per well together with 100 μl of the 1/2 PD medium. Then these inoculation sources were incubated in a thermostat at 28° C. The growth of the fungi was monitored by measuring the absorbance at 595 nm with a microplate reader (Benchmark, Bio-Rad Co. Ltd.).

Effects of salt and buffer: The effects of salt and buffers on the growth of the fungi were determined by adding a definite amount of NaCl, a phosphate buffer, a Tris buffer, a Hepes buffer, bovine serum albumin, dithiothreitol, etc. to the media.

2) Extract of Proteins from *Lyophyllum Shimeji*

10 g of *Lyophyllum shimeji* (made in Japan, obtained from Shiga Forest Research Center) was preliminarily cut into small pieces with scissors, frozen by using liquid nitrogen and ground in a mortar to give small grains. Then the grains were extracted with 30 ml of a 50 mM Hepes buffer for 30 minutes. The extract was filtered through Miracloth and then centrifuged at 10,000×g for 20 minutes. Then ammonium sulfate was added to the super-natant to achieve 75% saturation and the mixture was allowed to stand at 4° C. overnight. After centrifuging at 15,000×g for 20 minutes again, the precipitate was dissolved in 3 ml of a 10 mM Hepes buffer (pH 7.5) and dialyzed against a 10 mM Hepes buffer (pH 7.5) using a dialysis tube (Spectra/Porl MWC06-8000, Spectrum Medical Industries Co. Ltd.) or a benzoylated dialysis tube (SIGMA Co. Ltd.). After removing the insoluble substances by centrifugation, a *Lyophyllum shimeji* protein sample was obtained. The protein concentration of the *Lyophyllum shimeji* protein sample was measured by the Bradford method using bovine serum albumin (BSA) as a standard protein.

Example 2

Purification of Antimicrobial Protein

1) Antimicrobial Activity of Crude *Lyophyllum Shimeji* Protein Sample

Immediately after starting incubation of *Pyricularia oryzae* and *Rhizoctonia solani*, a definite amount the crude *Lyophyllum shimeji* protein sample was added to the incubation systems. Then changes in the absorbance were monitored with the passage of time for 2 days and thus the presence or absence of the antimicrobial activity was determined. The protein sample was diluted in series so that the dilution limit concerning the antimicrobial activity was determined. As a result, high antimicrobial activity was found both on *Pyricularia oryzae* and *Rhizoctonia solani* (Table 1).

TABLE 1

Antimicrobial activity of crude *Lyophyllum shimeji* protein extract

| Mushroom | pH at extraction | Complete growth inhibitory concentration (μg/ml) | |
| --- | --- | --- | --- |
| | | *P. oryzae* | *R. solani* |
| *L. shimeji* | 7.5 | 30 | 30 |

Concentration of the protein extract form *Lyophyllum shimeji* necessary for the complete growth inhibitory against *Pyricularia oryzae* is roughly estimated as 30 μg or less of total extracted protein/ml. Thus, it became evident that the *Lyophyllum shimeji* extract contains a substance having a high antibacterial activity. Concerning the manner of growth inhibitory of this protein extract against the fungi, complete inhibition of germination was observed at high concentrations and the inhibition of the hypha growth was observed at low concentrations. The inhibition level of the hypha extension clearly depended on the concentration used. In *Pyricularia oryzae* cells, the cytoplasm was separated from the cell wall, thereby showing a plasmolysis-like state.

2) Purification by Ion Exchange Column Chromatography

Next, the antimicrobial protein was purified. 70 g of *Lyophyllum shimeji* was ground in liquid nitrogen and the protein was extracted in 200 ml of a buffer (50 mM MES, 50 mM NaCl, pH 6.0) for 30 minutes. After filtering though double-folded Miracloth, the filtrate was centrifuged at 15,000×g for 20 minutes to thereby precipitate impurities. The supernatant was further filtered through filer paper to give a protein sample. About 200 ml of the protein sample was poured into a column (1.1 cm in inner diameter, 20 cm in height) filled with an ion exchanger Q-Sepharose FF (Pharmacia Co. Ltd.). While controlling the flow rate to 2.5 ml/min, use was made of a 50 mM Mes (pH 6.0), 50 mM NaCl as the base buffer and 50 mM Mes (pH 6.0), 1 M NaCl as the elusion buffer. A gradient of 50 mM to 1 M of NaCl was applied from 100 to 120 minutes after loading the sample. Subsequently, the elution buffer was passed through for additional 40 minutes. Fractions were collected 4 times after the application of the gradient (100 ml/fraction). These 4 fractions (I, II, III and IV) were diluted in series and thus an antimicrobial assay aginst *Pyricularia oryzae* was performed. As a result, the fractions II to IV showed antimicrobial activities. These fractions caused the plasmolysis of the pathogenic fungal cells. The fraction II (corresponding to 0 to 333 mM NaCl) showing the highest activity was concentrated with Centriprep (Amicon Co. Ltd., MWCO 10,000) and poured into an ion exchange column Mono QHR 5/5 (Pharmacia Co. Ltd.) to thereby partially purify the antimicrobial protein. While controlling the flow rate to 1 ml/min, use was made of a 50 mM Mes (pH 6.0) and 50 mM NaCl as the base buffer and 50 mM Mes (pH 6.0), 1 M NaCl as the elusion buffer. A gradient of 50 mM to 1 M of NaCl was applied from 20 to 40 minutes after loading the sample. A portion of each fraction (1 ml) was subjected to an antimicrobial assay against *Pyricularia oryzae* and SDS-PAGE electrophoresis. FIG. 1 shows the relationship between the HPLC chart and the strength of the antimicrobial activity. The antimicrobial activity, which was measured by collecting 5, 1 and 0.2 μl portions from each MonoQ fraction and performing the antimicrobial assay against *Pyricularia oryzae*, is shown in 4 grades, i.e., +++ (inhibiting at 0.2 μl), ++ (inhibiting at 1 μl), + (inhibiting at 5 μl) and – (not inhibiting even at 5 μl). When the protein was monitored based on $A_{280}$ and the strength of the antimicrobial activity against *Pyricularia oryzae*, an elution peak of the antimicrobial protein appeared at around an ionic strength (NaCl concentration) of 250 mM at pH 6.0. Subsequently, the antimicrobial activity of the protein per unit eluate was gradually lowered with a concurrent increase in the ionic strength.

Next, an aliquot of a 10 μl from each fraction was added by an equivalent amount of a 2×SDS electrophoresis buffer (Sambrook et al. 1989). After treating at 95° C. for 5 minutes, SDS-PAGE electrophoresis was performed in accordance with the method of Laemmli (1970). As the gel, use was made of a 15% PAGEL (ATTO Co. Ltd.) and the protein was detected with the use of a silver-staining II Kit Wako (Wako Pure Chemical Industries, Ltd.). To roughly estimate the molecular weight and amount of the protein, molecular weight markers (LMW, manufactured by Pharmacia LKB Co. Ltd., 94 kDa, 67 kDa, 43 kDa, 30 kDa, 20.1 kDa and 14.4 kDa, descending from larger to smaller size) were electrophorased in such a manner that a single band stood for 20 ng. FIG. 2 shows the relationship between the electrophoretic pattern and the strength of the antimicrobial activity. The numbers given above the lanes correspond respectively to the fraction numbers in FIG. 1. The strength of the antimicrobial activity is shown as in FIG. 1. Intensive studies revealed that two bands of about 70 kDa and about 65 kDa are considered as candidates for the protein relating to the antimicrobial activity (arrows in FIG. 2). Since the concentrations of these two bands positively correlate to the antimicrobial activity level, it is strongly suggested that these bands correspond to the antimicrobial protein(s) per se. Among these bands, the one of 65 kDa shows a clear link between protein band density and antimicrobial activity both in the Q-Sepharose fraction and in the MonoQ fraction. Considering from a molecular weight marker (albumin of 67 kDa), the amount of the antimicrobial protein was estimated with a densitometer and thus concentration necessary for the complete growth inhibitory against *Pyricularia oryzae* was calculated as about 5 ng/ml.

3) Determining N-end Amino Acid Sequence of Antimicrobial Protein

The monoQ fraction Nos. 36 to 44 were concentrated with Centrlfut V-20 (Kurabo Industries, Ltd.) and subjected to SDS-PAGE electrophoresis. After eliminating Tris, the separated proteins were transferred onto a PVDF membrane (Millipore Co. Ltd.) in a glycine-free buffer system, lightly stained with Coomassie Brilliant Blue and decolored. Next, the protein bands of 70 kDa and 65 kDa, which are considered to correspond to the antimicrobial proteins were excited from the membrane. The N-end amino acid sequences were determined by the Edman method with the use of a gas phase protein sequencer (HPG1005A Protein Sequencing System).

Consequently, the following 30 amino acids of the 65 kDa protein were determined.

N'-NAEEGTAVPYVPGYHKKNEIEFQKDIDRFV-C' (SEQ ID NO:3)

On the other hand, the 70 kDa protein could not be sequenced. The reason seems to be that the protein was blocked at the N'-end. Therefore, the 70 kDa protein was partially digested with the use of lysylendopeptidase and V8 protease to give 43 kDa of a lysylendopeptidase-digestion product and 45 kDa of a V8 protease-digestion product. By reanalyzing the amino acid sequences of these partially digested proteins, the following 24 residues and 29 residues were determined respectively from the former and latter proteins.

N'-EFDESIRHTLVLRSLQDAYKDRQR-C' (SEQ ID NO:4) and

N'-AERLIGTSTKEFDESIRHTLVLRSLQDAY-C' (SEQ ID NO:5).

Since these amino acid sequences mostly overlapped with each other, the internal amino acid sequence of 34 residues in total have been thus determined.

N'-AERLIGTSTKEFDESIRHTLVLRSLQDAYKDRQR-C' (SEQ ID NO:6).

The amino acid sequences thus determined were searched for in a data base. As a result, the 30 amino acids from the 65 kDa protein and the 34 amino acids from the 70 kDa protein both showed homology with pyranose oxidase of *Coriolus versicolor*. Thus, the pyranose oxidase activity of each MonoQ fraction was measured in accordance with the method of Nishimura et al. (1996). As a result, it was found that the pyranose oxidase activity strength was concurrent with that as could be expected from the antimicrobial activity strength. Accordingly, it is estimated that the antimicrobial activity would be derived from hydrogen peroxide formed during the oxidation of glucose in the medium by this enzyme. Next, the fractions containing both of the 65 kDa and 70 kDa proteins (FIG. 2 Nos. 42–44) were exclusively concentrated and properties of pyranose oxidase were analyzed. As a result, it was revealed that these fractions showed very high pyranose oxidase activity and low Km values to glucose and 1,5-anhydroglucitol (Table 2).

TABLE 2

Pyranose oxidase activity of the antimicrobial
protein of *L. shimeji* and various properties thereof

| Enzyme protein | Km (mM) Glucose | Km (mM) 1,5-Anhydroglucitol | Specific activity (U/mg)* |
|---|---|---|---|
| L. shimeji | 0.50 | 6.5 | 10.6 |

*1U = 1 μmole $H_2O_2$/min, pH 7.0, 37° C.

The amount of the enzyme proteins (65 kDa+70 kDa) was determined by SDS-PAGE silver staining.

Example 3

Isolation of cDNA

1) Design of Degenerate Primers

Based on the amino acid sequences determined in 1), primers comprising mixtures of all of potential bases were synthesized (Tm: 52 to 56° C., Numbers in the parentheses mean each the degree of degeneracy). More specifically, the following three primers were synthesized from the amino acid sequence (30 residues) originating from the 65 kDa protein:

65R1 (5'-gargarggiacigcigticc-3' (4)) (SEQ ID NO:7);
65R2 (5'-garttycaraargayathgaymg-3' (384)) (SEQ ID NO:8); and
65R3 (5'-ttygtiaaygtiathtgyggigc-3' (24)) (SEQ ID NO:9).

On the other hand, the following three primers were synthesized from the amino acid sequence (34 residues) originating from the partial digestion products of the 70 kDa protein:

70F1 (5'-tgickdatiswytcrtcraaytc-3' (384)) (SEQ ID NO:10);
70F2 (5'-tgickrtcyttrtaigcrtcytg-3' (64)) (SEQ ID NO:11); and
70F3 (5'-ggigcraadatickytgickrtc-3' (96))(SEQ ID NO:12).

In the above-described primers, r means a or g; y means c or t; h means a, c or t; m means a or c; k means g or t; d means a, g or t; s means g or c; w means a or t; and i means inosine.

2) Construction of cDNA Library from *Lyophyllum Shimeji* Fruit Body

Total nucleic acid was extracted from *Lyophyllum shimeji* fruit body by the SDS phenol method and total RNA was recovered by lithium chloride precipitation. Then *Lyophyllum shimeji* mRNA was prepared therefrom by using an mRNA purification kit (Pharmacia Co. Ltd.). Thus 20 μg of mRNA was obtained from about 10 g of the fruit body. A 5 μg of the mRNA was used for ZAP cDNA Synthesis Kit (Stratagene Co. Ltd.) to synthesize cDNA. 1 to 5 kb cDNA fractions were collected by using a gel filtration column, ligated to a Uni-ZAP XR vector (Stratagene Co. Ltd.) and then packaged into Gigapack III (Stratagene Co. Ltd.). All procedures were carried out in accordance with the manufacturer's instruction attached to the kits. The titer of *Lyophyllum shimeji* cDNA library thus constructed was calculated as about 3,000,000 pfu.

3) Preparing the Probe by RT-PCR

By using the primers synthesized in 1), PCR was carried out with the use of the cDNA synthesized in 2) as a template, thereby trying to amplify the partial length cDNA of the *Lyophyllum shimeji* protein which can be used as a probe for screening the library. The reaction condition employed were as follows. 50 μl of the reaction mixture solution contained 100 ng of cDNA, 5 μl of 10×Eq taq buffer, 4 μl of dNTPs, 10 pmoles/each kind of sequence of the primer and 1 μl of Ex taq (Takara Shuzo Co. Ltd.)+Taq START antibody (Clontech Co. Ltd.). By using Program Temp Control System PC-700 (ASTEK Co. Ltd.), the PCR consisted of 3 minutes at 94° C. once, 35 cycles of 1 minute at 94° C., 1 minute at 50° C. and 1 minute at 72° C., and then 6 minutes at 72° C. once. As a result, products of about 0.4 to 0.5 kb were amplified with the primer combinations of 65R1-70F1, 65R1-70F2, 65R2-70F1, 65R2-70F2, 65R2-70F3 and 65R3-70F1. Among them, an about 0.4 kb fragment showing a higher amplification efficiency was gel-purified and cloned into a vector PCRII (manufactured by Invitrogen) thereby determine the base sequence. The amino acid sequence deduced on the basis of this base sequence contained the same sequence as a part of the amino acid sequence determined in Example 2–3) and the entire sequence showed a mild homology with *Coriolus versicolor* pyranose oxidase. Based on these results, it has been confirmed that the purified antimicrobial proteins of 70 kDa and 65 kDa are coded by a single gene and the cDNA clone obtained by the RT-PCR is a partial length cDNA of the *Lyophyllum shimeji* antimicrobial protein.

4) Screening of the Full Length cDNA

The clone obtained in 3) was excised from the vector and employed as a probe for screening the *Lyophyllum shimeji* cDNA library constructed in 2). In a square Petri dish (14×10 cm), about 15,000 pfu of the phage was plated together with a host XL1-blue MRF' in accordance with the manufacture's instruction attached to ZAP cDNA Synthesis Kit (Stratagene Co. Ltd.). Then the plaque was brought into contact with a nylon membrane filter Hybond-N+ (Amersham Co. Ltd.) and treated with an alkali in accordance with the manufacturer's instruction attached to the membrane. Thus, in order to denature the DNA and fix them on the membrane. Hybridization and washing were performed under highly stringent conditions in accordance with the manufacturer's instruction attached to the membrane. In the primary screening, 20 positive clones were obtained from about 120,000 pfu of the phage. These clones were subjected to the secondary screening and then the tertiary screening which also aimed at purifying the plaques. All of these 20 clones were subjected to in vivo excision in accordance with the manufacturer's instruction attached to ZAP cDNA Synthesis Kit (Stratagene Co. Ltd.). As a result, 18 clones were collected as cDNA integrated in the phagemid vector pBluescript SK. These clones were 1.7 to 2.1 kb in length. The analysis with restriction enzymes suggested that these clones might originate from genes closely similar to each other.

5) Determination of Base Sequence

Concerning the 18 cDNA clones as described above, the 5'- and 3'-side base sequences (about 500 bp each) were determined. The base sequence data thus obtained were analyzed with the use of an analysis soft Genetyx ver. 9.0 (Software Development Co. Ltd.). As a result, all of these clones contained the DNA sequence encoding the 30 amino acids of the 65 kDa protein determined in Example 2–3), though the poly A addition site differed from clone to clone. The full base sequence of the longest cDNA clone No. 13 (2.1 kb) was determined by the primer walking method with the use of ABI PRIMS Fluorescence Sequencer (Model 1310 Genetic Analyzer, Perkin Elmer Co. Ltd.). As a result, the cDNA encoding the *Lyophyllum shimeji* antimicrobial protein consisted of 2106 base pairs in full length, and contains an open reading frame of 1854 bp encoding 618 amino acids (SEQ ID Nos:1 and 2). Based on the amino acid sequence, the molecular weight was estimated as about 68487 and the isoelectric point was calculated as 6.12. In the amino acid sequence determined from the purified protein, the 30 amino acids originating from the 65 kDa protein corresponded to the amino acids residues Nos. 76 to 105 in SEQ ID NO:2, and the 34 amino acids originating from the 70 kDa protein correspond to the amino acids residues Nos. 211 to 244 therein. These facts indicate that the 65 kDa and 70 kDa proteins are coded by a single gene. Further, there were 7 positions estimated as sugar chain attachment sites (amino acid residues Nos. 154, 319, 360, 412, 558, 573 and 583 in SEQ ID NO:2).

Based on these results, it is concluded that the cloned cDNA originates from a gene encoding the *Lyophyllum shimeji* antimicrobial protein. The homology of the amino acid sequence of the *Lyophyllum shimeji*-origin antimicrobial protein according to the present invention was searched for (BLAST) on data base (DDBJ). As a result, it showed a 45% identity as the whole with the amino acid sequence of *Coriolus versicolor* pyranose oxidase. Since there was no other homologous sequence, this gene is presumed to encode a novel pyranose oxidase-like protein.

Example 4

Expression in *E. coli* and Purification of Recombinant Protein

1) Construction of an Expression Vector

The cDNA clone No. 13 isolated in Example 3–5) carries a unique EcoT22I restriction site about 0.06 kb downstream of the termination codon and a unique BamHI restriction site about 0.25 kb upstream of the termination codon. Also, BamHI is located at the multicloning site on the 5'-side vector of this cDNA. First, a plasmid having this cDNA integrated therein (vector: pBluescript) was completely digested with a restriction enzyme EcoT22I (Takara Shuzo, Co. Ltd.) and then partially digested with BamHI (manufactured by Takara). The about 2 kb BamHI (BamHI on the vector)-EcoT22I fragment thus formed was integrated into an expression vector for *E. coli* pQE30 (Qiagen, Co. Ltd.) which has been double-digested with restriction enzymes BamHI and PstI (named pQEHSPOfull). The construct thus formed contained the longest open reading frame (ORF) of the full length cDNA encoding the *Lyophyllum shimeji* pyranose oxidase-like protein according to the present invention (containing the base sequence of Nos. 8 to 1864 in SEQ ID NO:1, encoding the full amino acid sequence of SEQ ID NO:2 in the Sequence Listing) and 6 histidine residues were attached to the N'-end of the expressed protein as tags.

2) Expression in *E. Coli*

An expression experiment was carried out by using *E. coli* M15 strain as a host. The incubation of the strain and the induction of the protein expression by IPTG (isopropyl β-D-thiogalactopyranoside) were carried out in accordance with the manufacturer's instruction (Qiagen). The strain was pre-incubated in an LB medium containing antibiotics ampicillin and kanamycin until $OD_{600}$ reached about 0.5. Subsequently, it was incubated in the same medium at various temperatures and at various IPTG concentrations for a definite time to thereby induce the expression. Soluble proteins were extracted in accordance with the manufacturer's instruction (Qiagen) and a definite amount thereof was subjected to the measurement of the pyranose oxidase activity in accordance with the method of Nishimura et al. (1996). Table 3 summarizes the results of the expression of the recombinant protein.

TABLE 3

Expression of *Lyophyllum shimeji* pyranose oxidase in *E. coli*

| Construct | Induction condition | | Pyranose oxidase activity (mU/mL culture) | |
|---|---|---|---|---|
| | Temp. (° C.) | IPTG (mM) | After 5 h | After 21 h |
| pQEHSPOful | 37 | 2 | 0 | 0 |
| | 25 | 0.5 | 2.5 | 1 |
| | 16 | 0.1 | 15 | 34 |
| pQE30 (control) | 25 | 0.5 | 0 | 0 |
| | 16 | 0.1 | 0 | 0 |

Although induction was first attempted under usual conditions (37° C., IPTG concentration 2 mM), no pyranose oxidase activity was detected in the soluble fraction but a large amount of insoluble inclusions were expressed. Then the expression was induced under various conditions and the pyranose oxidase activity in the soluble fraction was measured. As a result, the pyranose oxidase activity was elevated as the induction conditions became mild, i.e., lowering the culture temperature and decreasing the IPTG concentration. It seems because the content of the soluble recombinant protein was increased as the induction conditions became mild. In contrast, no activity was detected from pQE30 (vector alone) employed as the control. These results clearly indicate that the cloned cDNA certainly encodes the active pyranose oxidase-like protein. In the incubation at 25° C. at IPTG concentration of 0.5 mM, a decrease in the activity was observed 21 hours after, compared with 5 hours after the induction start. It seems because the expressed protein had been decomposed.

Next, an attempt was made to purify the expressed protein. From the soluble protein fraction originating in the cells under the induction of the expression at 16° C. at IPTG concentration of 0.1 mM, the recombinant pyranose oxidase-like protein was purified by using Ni-NTA Agarose (Qiagen, Co. Ltd.). The protein was adsorbed, washed and eluted in accordance with the manufacturer's instruction (Qiagen). As a result, the pyranose oxidase activity was found only in the eluted fraction. It has been thus revealed that the N'-end of the recombinant protein was not digested in *E. coli*, and the histidine residues were still attached to the N'-end; that the recombinant protein can be easily purified by Ni-NTA Agarose by taking advantage of the histidine residues; and that the coding domain of the cloned full length cDNA are encoding the active protein as such (i.e., without removing a portion corresponding to the N-end side of the protein). The yield of the recombinant protein was estimated as several mg per 1 litter of the *E. coli* culture broth.

Effects

It is expected that a formulation comprising as an active ingredient, a protein component characterized by having the sequence of SEQ ID NO:2 in the Sequence Listing according to the present invention, or the full length thereof but excluding the sequence of Nos. 1 to 75, can be used as a potent antibacterial agent. Moreover, a reagent containing the above-described protein component as the active ingredient can be used for measuring sugars such as blood sugar level. It is expected that a plant tolerant to disease and pests can be constructed by integrating, a DNA sequence characterized by the sequence of Nos. 8 to 1864, or the sequence of Nos. 233 to 1864 in the DNA sequence of SEQ ID NO:1-in the Sequence Listing, into an expression cassette, said cassette comprises a constitutive, organ/time-specific or stress-inducible or disease/insect-inducible promoter sequence capable of functioning in plant cells and a terminator sequence capable of functioning in plant cells, transferring the cassette into a plant cell and obtaining a regenerated individual. Moreover, the protein can be obtained in a large amount by transferring the above-described DNA sequences into E. coli, yeasts, insects or certain animal cells by using an expression vector capable of amplifying in the host selected and, expressing the protein.

What is claimed is:

1. An isolated nucleic acid encoding an antimicrobial protein having pyranose oxidase activity,
   wherein said antimicrobial protein has an amino acid sequence of SEQ ID NO:2, or has 80% or more identity with said sequence and has an antimicrobial activity against *Rhizoctonia solani* or *Pyricularia oryzae*; or
   wherein said protein comprises an amino acid sequence of amino acid residues 76 to 618 of SEQ ID NO:2, or a polypeptide having 80% or more identity with said amino acid sequence and having an antimicrobial activity against *Rhizoctonia solani* or *Pyricularia oryzae*.

2. The isolated nucleic acid according to claim 1, encoding an antimicrobial protein and having a base sequence of SEQ ID NO:1, or a base sequence which is complementary to a base sequence which hybridizes to SEQ ID NO:1 under stringent conditions of 6× SSC, (without formamide).

3. The isolated gene nucleic acid according to claim 1 encoding a protein having antimicrobial activity and having an 80% or more identity with the base sequence of SEQ ID NO:1.

4. The isolated nucleic acid according to claim 1 encoding a protein having antimicrobial activity and having a 90% or more identity with the base sequence of SEQ ID NO:1.

5. The isolated nucleic acid according to claim 1 encoding a protein having antimicrobial activity and having a 95% or more identity with the base sequence of SEQ ID NO:1.

6. A recombinant vector containing the isolated nucleic acid according to claim 1.

7. The recombinant vector according to claim 6 wherein said vector is an expression vector.

8. A transformed microorganism obtained by introducing the recombinant vector according to claim 6 into a host organism.

9. An isolated nucleic acid encoding an antimicrobial protein having pyranose oxidase activity and having a base sequence of SEQ ID NO:1, or a base sequence which is complementary to a base sequence which hybridizes to SEQ ID NO:1 under stringent conditions of 6× SSC, (without formamide).

10. An isolated nucleic acid encoding an antimicrobial protein having pyranose activity, wherein said protein can be obtained from a fraction of an aqueous extract of *Lyophyllum shimeji* precipitated by the ammonium sulfate precipitation method, and wherein said protein has an antimicrobial activity at least against *Rhizoctonia solani* or *Pyricularia oryzae*, and shows the presence of components of about 70 kDa and/or about 65 kDa in molecular weight in the SDS-PAGE method.

11. An isolated nucleic acid encoding an antimicrobial protein having pyranose oxidase activity, wherein said protein can be obtained from a fraction of an aqueous extract of *Lyophyllum shimeji* precipitated by the ammonium sulfate precipitation method, and wherein said protein has an antimicrobial activity at least against *Rhizoctonia solani* or *Pyricularia oryzae*, and shows the presence of components of about 70 kDa and/or about 65 kDa in molecular weight in the SDS-PAGE method; and wherein said nucleic acid has a base sequence of SEQ ID NO:1 or a base sequence which is complementary to a base sequence which hybridizes to SEQ ID NO:1 under stringent conditions of 6× SSC, (without formamide).

12. The isolated nucleic acid according to claim 1 encoding an antimicrobial protein, wherein said antimicrobial protein has an amino acid sequence of SEQ ID NO:2 or has 90% or more identity with the amino acid sequence of SEQ ID NO:2.

13. The isolated nucleic acid according to claim 1 encoding an antimicrobial protein, wherein said antimicrobial protein has an amino acid sequence of SEQ ID NO:2 or has 95% or more identity with the amino acid sequence of SEQ ID NO:2.

14. The isolated nucleic acid according to claim 1 encoding an antimicrobial protein, wherein said antimicrobial protein has an amino acid sequence of SEQ ID NO:2 or has 80% or more identity with the amino acid sequence of SEQ ID NO:2 by a substitution of one or more amino acids of SEQ ID NO:2, wherein the substitution of one or more amino acids of SEQ ID NO:2 replaces a hydrophobic amino acid with a hydrophobic amino acid, a hydrophilic amino acid with a hydrophilic amino acid, an acidic amino acid with an acidic amino acid or a basic amino acid for a basic amino acid.

15. The isolated nucleic acid according to claim 1 encoding an antimicrobial protein, wherein said antimicrobial protein has an amino acid sequence of SEQ ID NO:2 or has 90% or more identity with the amino acid sequence of SEQ ID NO:2 by a substitution of one or more amino acids of SEQ ID NO:2, wherein the substitution of one or more amino acids of SEQ ID NO:2 replaces a hydrophobic amino acid with a hydrophobic amino acid, a hydrophilic amino acid with a hydrophilic amino acid, an acidic amino acid with an acidic amino acid or a basic amino acid for a basic amino acid.

16. The isolated nucleic acid according to claim 1 encoding an antimicrobial protein, wherein said antimicrobial protein has an amino acid sequence of SEQ ID NO:2 or has 95% or more identity with the amino acid sequence of SEQ ID NO:2 by a substitution of one or more amino acids of SEQ ID NO:2, wherein the substitution of one or more amino acids of SEQ ID NO:2 replaces a hydrophobic amino acid with a hydrophobic amino acid, a hydrophilic amino acid with a hydrophilic amino acid, an acidic amino acid with an acidic amino acid or a basic amino acid for a basic amino acids.

* * * * *